(12) United States Patent
He et al.

(10) Patent No.: US 11,221,320 B2
(45) Date of Patent: Jan. 11, 2022

(54) METHOD AND APPARATUS FOR MEASURING LEAF NITROGEN CONTENT

(71) Applicant: Zhejiang University, Hangzhou (CN)

(72) Inventors: Yong He, Hangzhou (CN); Zhengjun Qiu, Hangzhou (CN); Lei Zhou, Hangzhou (CN); Nan Zhao, Hangzhou (CN)

(73) Assignee: Zhejiang University, Hangzhou (CN)

( * ) Notice: Subject to any disclaimer, the term of this patent is extended or adjusted under 35 U.S.C. 154(b) by 85 days.

(21) Appl. No.: 16/878,856

(22) Filed: May 20, 2020

(65) Prior Publication Data

US 2021/0018480 A1 Jan. 21, 2021

(30) Foreign Application Priority Data

Jul. 17, 2019 (CN) .......................... 201910645516.4

(51) Int. Cl.
*G06K 9/00* (2006.01)
*G01N 33/00* (2006.01)
(Continued)

(52) U.S. Cl.
CPC ......... *G01N 33/0098* (2013.01); *G01N 21/17* (2013.01); *G06N 3/08* (2013.01);
(Continued)

(58) Field of Classification Search
CPC ............... G01N 33/0098; G01N 21/17; G01N 2021/1765; G01N 2021/8466;
(Continued)

(56) References Cited

U.S. PATENT DOCUMENTS 6,683,970 B1 * 1/2004 Satake .................. G01N 21/31
348/89
2017/0213083 A1 * 7/2017 Shriver ................ G01N 33/025
(Continued)

OTHER PUBLICATIONS

Watchareeruetai, Ukrit, et al. "Identification of plant nutrient deficiencies using convolutional neural networks." 2018 International Electrical Engineering Congress (iEECON). IEEE, 2018. (Year: 2018).*

(Continued)

*Primary Examiner* — Avinash Yentrapati
(74) *Attorney, Agent, or Firm* — Troutman Pepper Hamilton Sanders LLP; Christopher C. Close, Jr.

(57) ABSTRACT

The present invention discloses a method and an apparatus for measuring leaf nitrogen content (LNC), and belongs to the spectral analysis and artificial intelligence (AI) field. The method includes the following steps: (1) obtaining a single-band image of a target leaf illuminated by a light source in a single feature band; (2) repeating step (1), to collect image information in four feature bands; (3) combining the collected images in the four feature bands into a four-channel spectral image; (4) training a deep learning model by using the spectral image and a corresponding nitrogen content label, to obtain a nitrogen content prediction model; (5) transplanting the trained nitrogen content prediction model into an AI control system; (6) collecting information about a to-be-predicted leaf sample, predicting nitrogen content by using an AI sensor equipped with the AI control system, and outputting the predicted nitrogen content.

1 Claim, 4 Drawing Sheets

(51) Int. Cl.
  *G06T 7/00* (2017.01)
  *G01N 21/17* (2006.01)
  *G06N 3/08* (2006.01)
  *H04N 5/30* (2006.01)

(52) U.S. Cl.
  CPC .............. *G06T 7/0014* (2013.01); *G06T 7/97* (2017.01); *H04N 5/30* (2013.01); *G01N 2021/1765* (2013.01); *G06T 2207/20081* (2013.01); *G06T 2207/20084* (2013.01); *G06T 2207/30188* (2013.01)

(58) Field of Classification Search
  CPC ... G01N 2223/621; G06T 7/97; G06T 7/0014; G06T 2207/20081; G06T 2207/20084; G06T 2207/30188; G06N 3/08; H04N 5/30
  See application file for complete search history.

(56) References Cited

U.S. PATENT DOCUMENTS

| | | | |
|---|---|---|---|
| 2018/0373932 A1* | 12/2018 | Albrecht | G06F 17/14 |
| 2020/0126232 A1* | 4/2020 | Guo | G06N 3/0445 |
| 2020/0134358 A1* | 4/2020 | She | G06N 20/20 |
| 2020/0163296 A1* | 5/2020 | Panda | G06N 3/0445 |
| 2020/0359550 A1* | 11/2020 | Tran | G06T 7/0004 |

OTHER PUBLICATIONS

"Multispectral image estimation model study of rape nitrogen", Zhang Xiaodong et al., Chinese Agricultural Science, vol. 44, No. 16, pp. 3323-3332, Dec. 2011.

* cited by examiner

METHOD AND APPARATUS FOR MEASURING LEAF NITROGEN CONTENT

CROSS REFERENCE TO RELATED APPLICATIONS

This application claims priority, and benefit under 35 U.S.C. § 119(e) of Chinese Patent Application No. 201910645516.4 filed 17 Jul. 2019. The disclosure of the prior application is hereby incorporated by reference as if fully set forth below.

TECHNICAL FIELD

The present invention relates to the spectral analysis and artificial intelligence (AI) field, and specifically, to a method and an apparatus for measuring leaf nitrogen content (LNC).

BACKGROUND

LNC is one of important indicators reflecting the growth status of a plant. LNC measurement helps to determine a nutritional status of the plant, and can provide guidance on an artificial fertilization decision.

A conventional LNC measurement method is mainly a destructive chemical detection method, and manual operations need to be performed in a laboratory, wasting time and energy. With the development of the spectral analysis technology, the spectral analysis technology is widely applied in detecting crop information. In current research, usually, a large spectrograph is used to measure physiological indexes of the plant, and achieves a good effect. However, because the device has a large size, high cost, large data amount, difficult information storage and processing, etc, there is a high limitation of actual application of the device. It is found in the research that the LNC is closely related to chlorophyll content of the plant leaf, and the chlorophyll content may reveal the LNC. Briefly, the green degree of the plant leaf may be well used to calculate the nitrogen content. An existing handheld device usually used to detect the LNC is a soil and plant analyzer development (SPAD) instrument. The LNC is calculated by using strength of transmitted light signals of two bands (green light and near-infrared light).

The SPAD instrument is designed based on the spectral technology. In the laboratory, a large spectrum instrument is used to scan a to-be-detected sample to obtain spectral data; a regression model is used to establish a mathematical model between spectral reflectance or absorptivity under each wavelength and a physiological index, to select a characteristic wavelength that is most highly related to the nitrogen content, to detect a signal, and then select a wavelength of the near-infrared band lowly related to the LNC, to cancel impact caused by leaf thickness to detection. A detection system including only light sources of two bands and a sensing unit can accurately estimate the LNC, and has low costs. However, a detection apparatus designed based on a transmission method has the following problem: An excitation light source and a sensing and detection unit need to be disposed on opposite sides of a leaf; and therefore, during actual application, the leaf needs to be clamped for detection, troubling rapid and automatic detection. In addition, a detection means based on a spectral camera is easily interfered with by factors such as ambient light, a detection distance, and dust attached onto a surface of a leaf, and has high costs.

SUMMARY

An objective of the present invention is to provide a method for measuring LNC, to overcome a problem that LNC currently cannot be obtained automatically and rapidly.

Another objective of the present invention is to provide an apparatus for measuring LNC. The apparatus can automatically and rapidly obtain LNC.

To achieve the foregoing objective, the present invention provides a method for measuring LNC, where the method includes the following steps:

(1) obtaining a single-band image of a target leaf illuminated by a light source in a single feature band;

(2) repeating step (1), to collect image information in four feature bands;

(3) combining the collected images in the four feature bands into a four-channel spectral image;

(4) training a deep learning model by using the spectral image and a corresponding nitrogen content label, to obtain a nitrogen content prediction model;

(5) transplanting the trained nitrogen content prediction model into an AI control system;

(6) collecting information about a to-be-predicted leaf sample, predicting nitrogen content by using an AI sensor equipped with the AI control system, and outputting the predicted nitrogen content;

(7) outputting a nitrogen content prediction result through a serial port; and (8) displaying a distribution diagram of nitrogen content of leaves at different locations on a farmland.

Preferably, in step (2), the four feature bands are 490 nm to 500 nm, 590 nm to 600 nm, 630 nm to 640 nm, and 680 nm to 690 nm.

Preferably, the deep learning model in step (4) includes four convolutional blocks and a fully-connected network, where each convolutional block includes a convolutional layer, a rectified linear unit (ReLU) activation function, and a maximum pooling layer; the convolutional layer has a 3*3 convolutional kernel and a step length of 1; a size of the maximum pooling layer is 3*3, and a step length is 2; the fully-connected network includes two layers with 256 and 64 neurons respectively.

To achieve the other objective, the present invention provides an apparatus for measuring LNC, including: four groups of light emitting diodes (LED) providing light sources of feature wavelengths, a spectral imaging sensor, a light shield, an AI control system, and a peripheral circuit. The AI control system is obtained by using the following steps:

(1) obtaining a single-band image of a target leaf illuminated by a light source in a single feature band;

(2) repeating step (1), to collect image information in four feature bands;

(3) combining the collected images in the four feature bands into a four-channel spectral image;

(4) training a deep learning model by using the spectral image and a corresponding nitrogen content label, to obtain a nitrogen content prediction model; and (5) transplanting the trained nitrogen content prediction model into the AI control system The light shield may cover a surface of a to-be-detected sample, to prevent interference caused by ambient light to imaging. The four groups of LED light sources may be used as light sources of an imaging system, only one of the four groups of LED light sources is turned on each time, to illuminate a surface of the leaf, and a reflected light signal enters the spectral imaging sensor. In a shooting environment with the light shield and the LED light sources, the detected object is illuminated by a stable light source, and there is no need to perform complex background cancellation operation on an obtained image.

Compared with the prior art, the present invention has the following beneficial effects:

The apparatus in the present invention has a simple structure, a convenient operation, and low costs, and can provide an environment required by implementation of an algorithm. The apparatus of the present invention obtains a spectral image of a leaf, nitrogen content is predicted by using a deep convolutional neural network model, and data collection and calculation are implemented on a hardware platform of the present invention. The method in the present invention uses the spectral analysis technology, AI, and a local calculation hardware platform, and has advantages of low costs, high working efficiency, local calculation, and high accuracy, and there is no need to transmit data to a remote server through Internet for calculation and analysis.

DETAILED DESCRIPTION

To make the objectives, the technical solutions, and the advantages of the present invention clearer, the following further describes in detail the present invention with reference to examples and the accompanying drawings.

Example

Figure 1:
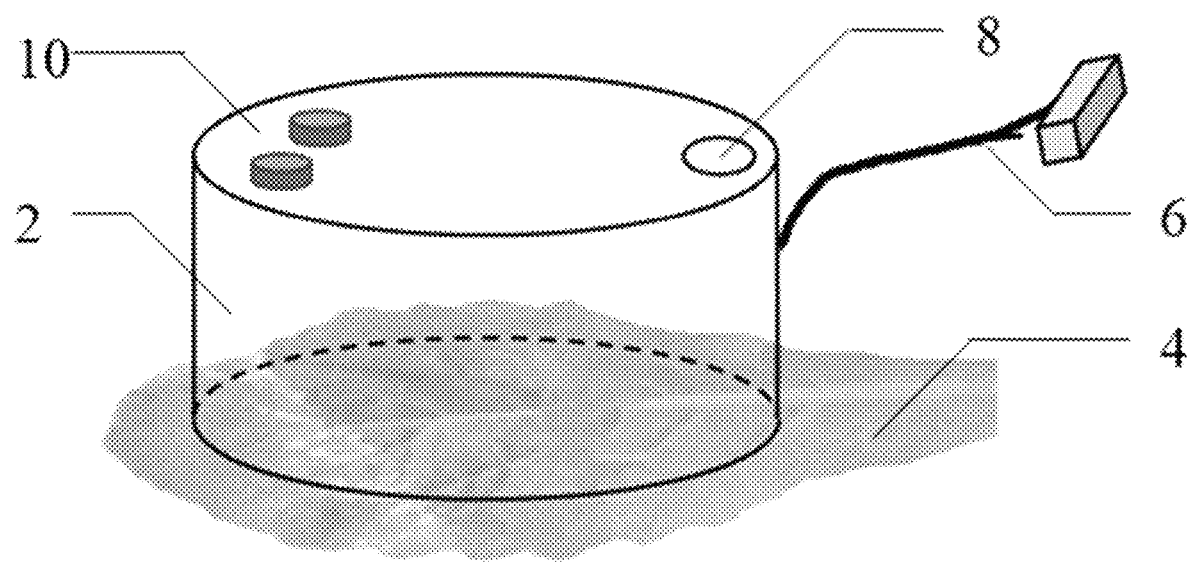
FIG. 1 is a schematic diagram of an overall structure of an apparatus for measuring LNC according to the present invention.
Figure 2:
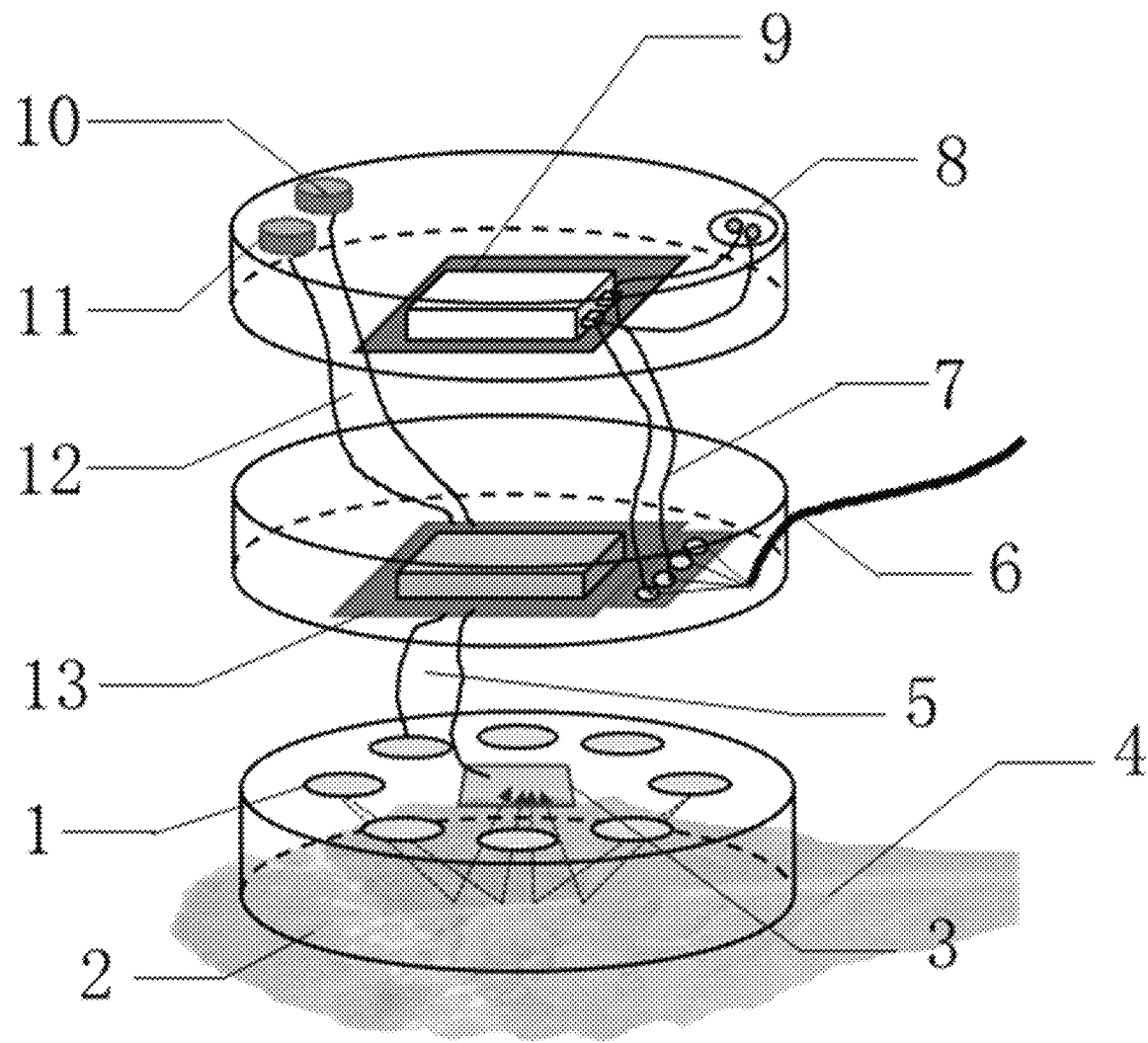
FIG. 2 is an exploded view of an apparatus for measuring LNC according to an example of the present invention.

Referring to FIG. 1 and FIG. 2, an apparatus for measuring LNC in this example includes LED light sources 1, a light shield 2, a dot-matrix spectral image sensor 3, a to-be-detected sample 4, a control signal line and power line 5 of the light sources and the dot-matrix spectral image sensor, a pigtail 6 of an output interface, a power supply line 7, a charging interface 8, a lithium battery and a peripheral circuit 9, a start button 10, a measurement button 11, a button signal line 12, and an AI control system 13.

The opening of the light shield 2 covers a surface of the to-be-detected sample 4, to form an imaging environment that is not interfered with by ambient light. The measurement button 11 is pressed, the AI control system 13 outputs a drive signal, one group of LED light sources is turned on, and after the light source is stable, a digital signal is read from the dot-matrix spectral image sensor 3. The other three groups of light sources are turned on according to the foregoing steps, and corresponding digital image information is obtained. The AI control system 13 combines the obtained digital signals into a four-channel dot-matrix spectral image, processes the four-channel dot-matrix spectral image by using an integrated deep convolutional neural network model, to obtain the LNC through calculation, and outputs the nitrogen content by using a serial port. An external device may access an output result of the sensor in this example through the pigtail 6 of the output interface.

Figure 3:
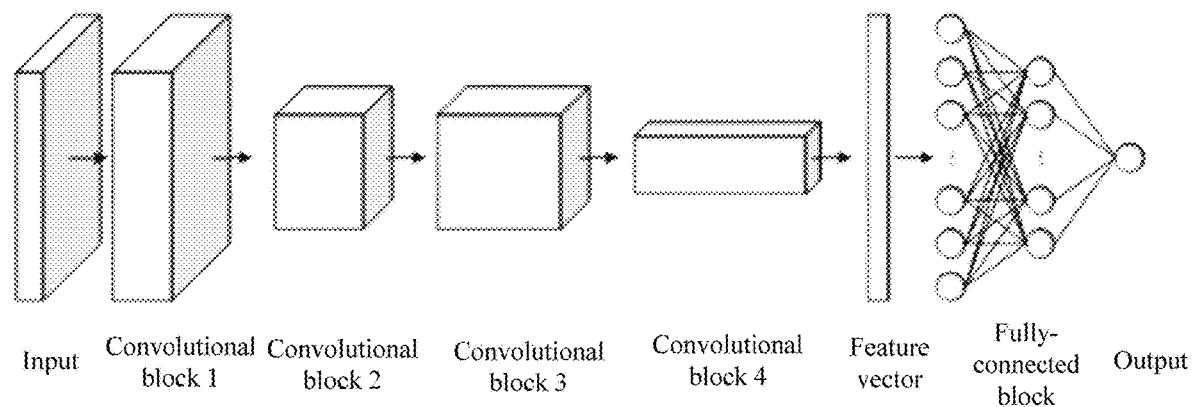
FIG. 3 is a structural diagram of a model of a used deep convolutional neural network according to an example of the present invention.
Figure 4:
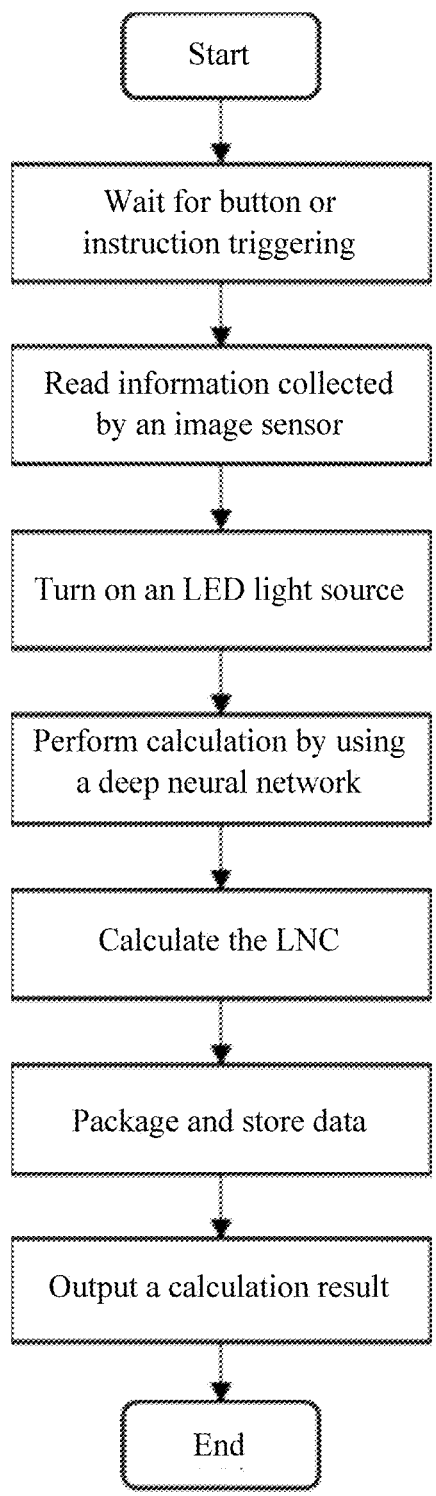
FIG. 4 is a working flowchart of an apparatus for measuring LNC according to an example of the present invention.

Referring to FIG. 4, the sensor in this example needs to perform algorithm processing on a dot-matrix image, including the following steps:

First step: Construct a deep convolutional neural network model. A large quantity of four-channel dot-matrix spectral images obtained through collection and corresponding nitrogen content of a to-be-detected leaf obtained by using a chemometrics method are stored into a personal computer (PC), to construct a training data set. Then, the deep convolutional neural network model shown in FIG. 3 is trained by using the training data set, and a layer-by-layer convolutional operation is used to automatically extract a spectral feature and a texture feature in a dot-matrix image, to obtain a feature matrix. Subsequently, a fully-connected network structure is introduced, to learn a mapping relationship between a feature matrix and nitrogen content.

The deep convolutional neural network model in this example includes four convolutional blocks and a fully-connected network. Each convolutional block includes a convolutional layer, a ReLU activation function, and a maximum pooling layer. The convolutional layer has a 3*3 convolutional kernel and a step length of 1. A size of the maximum pooling layer is 3*3, and a step length is 2. The fully-connected network includes two layers with 256 and 64 neurons respectively.

Second step: After the model is trained on the PC, transplant a structure and a weighting parameter of the model into an AI control system.

Third step: Encapsulate the sensor, collect a dot-matrix spectral image of a new sample, calculate nitrogen content by using the model cured into the AI control system, and output the nitrogen content.

A method for measuring LNC in this example includes the following steps:

(1) Obtain a single-band image of a target leaf illuminated by a light source in a single feature band.

(2) Repeat step (1), to collect image information in four feature bands.

(3) Combine the collected images in the four feature bands into a four-channel spectral image.

(4) Train a deep learning model by using the spectral image and a corresponding nitrogen content label, to obtain a nitrogen content prediction model.

(5) Transplant the trained nitrogen content prediction model into an AI control system.

(6) Collect information about a to-be-predicted leaf sample, predict nitrogen content by using an AI sensor provided with the AI control system, and output the nitrogen content.

(7) Output a nitrogen content prediction result through a serial port.

(8) Display a distribution diagram of nitrogen content of leaves at different locations on a farmland.

What is claimed is:

1. A method for measuring leaf nitrogen content (LNC), comprising the following steps:
   (1) obtaining a single-band image of a target leaf illuminated by a light source in a single feature band;
   (2) repeating step (1), to collect image information in four feature bands, wherein the four feature bands are 490 nm to 500 nm, 590 nm to 600 nm, 630 nm to 640 nm, and 680 nm to 690 nm;
   (3) combining the image information in the four feature bands into a four-channel spectral image;

(4) training a deep learning model by using a spectral image and a corresponding nitrogen content label, to obtain a nitrogen content prediction model, wherein the deep learning model comprises four convolutional blocks and a fully-connected network, wherein each convolutional block comprises a convolutional layer, a rectified linear unit (ReLU) activation function, and a maximum pooling layer; the convolutional layer having a 3*3 convolutional kernel and a step length of 1; the maximum pooling layer having a size of 3*3, and a step length of 2; and the fully-connected network comprising two layers with 256 and 64 neurons respectively;

(5) transplanting the nitrogen content prediction model into an artificial intelligence (AI) control system, wherein the AI control system is obtained by using the following steps: (i) obtaining a single-band image of a target leaf illuminated by a light source in a single feature band; (ii) repeating step (i) to collect image information in four feature bands; (iii) combining the image information in the four feature bands into a four-channel spectral image; (iv) training a deep learning model by using a spectral image and a corresponding nitrogen content label, to obtain a nitrogen content prediction model; and (v) transplanting the nitrogen content prediction model into the AI control system;

(6) collecting information about a to-be-predicted leaf sample, predicting nitrogen content by using an AI sensor equipped with the AI control system to provide a nitrogen content prediction result, and outputting the nitrogen content;

(7) outputting the nitrogen content prediction result through a serial port; and (8) displaying a distribution diagram of nitrogen content of leaves at different locations on a farmland.

* * * * *